| United States Patent [19] | [11] 3,978,166 |
|---|---|
| Hechenbleikner | [45] Aug. 31, 1976 |

[54] CYCLIC PHOSPHONATES

[75] Inventor: Ingenuin Hechenbleikner, West Cornwall, Conn.

[73] Assignee: Borg-Warner Corporation, Chicago, Ill.

[22] Filed: Apr. 7, 1975

[21] Appl. No.: 565,699

[52] U.S. Cl. .................. 260/927 R; 106/15 FP; 156/321; 156/327; 252/8.1; 260/928; 260/953; 260/969; 260/937; 260/961; 428/428; 428/921; 428/538
[51] Int. Cl.² ...................... E05F 11/00; C09J 3/00
[58] Field of Search ............ 156/327, 321, 99, 305, 156/325, 326; 428/428, 921, 920, 426, 538; 106/15 FP; 8/116 P; 252/8.1; 260/927 R, 961, 969, 937, DIG. 24, 928, 953

[56] References Cited
UNITED STATES PATENTS

| 2,586,884 | 2/1952 | Fontoy et al. | 428/921 |
|---|---|---|---|
| 3,053,878 | 9/1962 | Friedman et al. | 106/15 FP |
| 3,141,032 | 7/1964 | Friedman | 106/15 FP |

*Primary Examiner*—William A. Powell
*Assistant Examiner*—J. J. Gallagher
*Attorney, Agent, or Firm*—Cushman, Darby & Cushman

[57] ABSTRACT

Alcohols preferably having a pka below that of propanol-1 are heated with certain heterocyclic phosphites to give phosphonates and certain heterocyclic phosphonites, to give phosphinates. If small amounts of alcohols are employed, the products are generally polymeric in nature whereas if larger amounts of the alcohol are employed, there is generally ring opening to the simpler monomer, or isomerization to the phosphonate or phosphinate. The products are useful as fire retardants and as adhesives for glass. Pentaerythritol phosphite can be self-polymerized by such heating to form the adhesive polymer.

24 Claims, No Drawings

CYCLIC PHOSPHONATES

The present invention is directed to novel processes and the phosphonate phosphinate products obtained thereby involving reacting an alcohol preferably having a pKa value below that of propanol-1 with a cyclic phosphite or cyclic phosphonite. The cyclic phosphite or phosphonite can be monocyclic or bicyclic and can even be spirio in nature. If small amounts of alcohol are employed, e.g. 0.001 to 0.1 mole per mole of cyclic phosphite or phosphinite the products formed are normally self-polymerization polymers. In general the lower the amount of alcohol the higher the molecular weight of the polymer.

If higher amounts of alcohol are employed, e.g. stoichiometric amounts of alcohol or more preferably 2 moles (or even more) e.g. 10 moles per phosphite phosphorus atom then the product normally is simply the monomeric phosphonate formed by ring opening and addition of the alcohol. When the amount of alcohol is below stoichiometric but above 0.1 mole there is a tendency to form mixtures of the polymeric phosphonate and the monomeric phosphonate. Heating at 100°–140°C or even up to 150°C is generally employed for the ring-opening, phosphonate monomer forming reaction whereas somewhat higher temperatures of 160°–250°C are employed for the polymerization.

Both the monomeric and polymeric products of the invention are useful as fire retardant additives for polymers such as polyethylene, polypropylene, ethylene-propylene copolymers, polystyrene, etc. The polymers are also useful as adhesives for bonding glass to glass or glass to metal e.g. glass to steel or metal to metal, e.g. steel to steel. The monomers tested also were useful for this purpose but showed somewhat lesser strength as adhesives, e.g. for glass to glass.

The reaction of the present invention appears to be somewhat similar to the classic Michaelis-Arbuzov reaction between an alkyl halide and a phosphite. There is one significant difference. Neohalides do not undergo the Michaelis-Arbuzov reaction but neoalcohols do undergo the reaction.

It is known that trimethyl phosphite isomerizes by heating to 210°–215°C with methanol (Cason, J. Org. Chem. Vol. 23, Pages 1302–5 — 1958) to the corresponding phosphonate but that reaction does not involve a heterocyclic phosphite and requires a higher temperature than the present reaction. To a lesser extent the same phosphonate formation reaction occurs with triethyl phosphite and ethyl alcohol. Partial phosphonation occurred when triethyl phosphite was heated with methyl alcohol as well as some phosphate formation but no phosphonation occurred when the methyl alcohol was replaced by butyl alcohol.

In the present invention the alcohols employed preferably have a pKa below that of propanol. Thus there can be used allyl alcohol, methyl alcohol, ethyl alcohol, benzyl alcohol and 2,3-dibromopropanol. There can also be used diprimary glycols, e.g. ethylene glycol, trimethylene glycol, hexamethylene glycol and the like. The reaction goes more slowly with n-propanol or n-butanol, hence their use is not preferred. With alcohols of higher pKa the reaction does not go at all.

As heterocyclic phosphite and phosphonite esters there can be used as starting materials compounds of the formula:

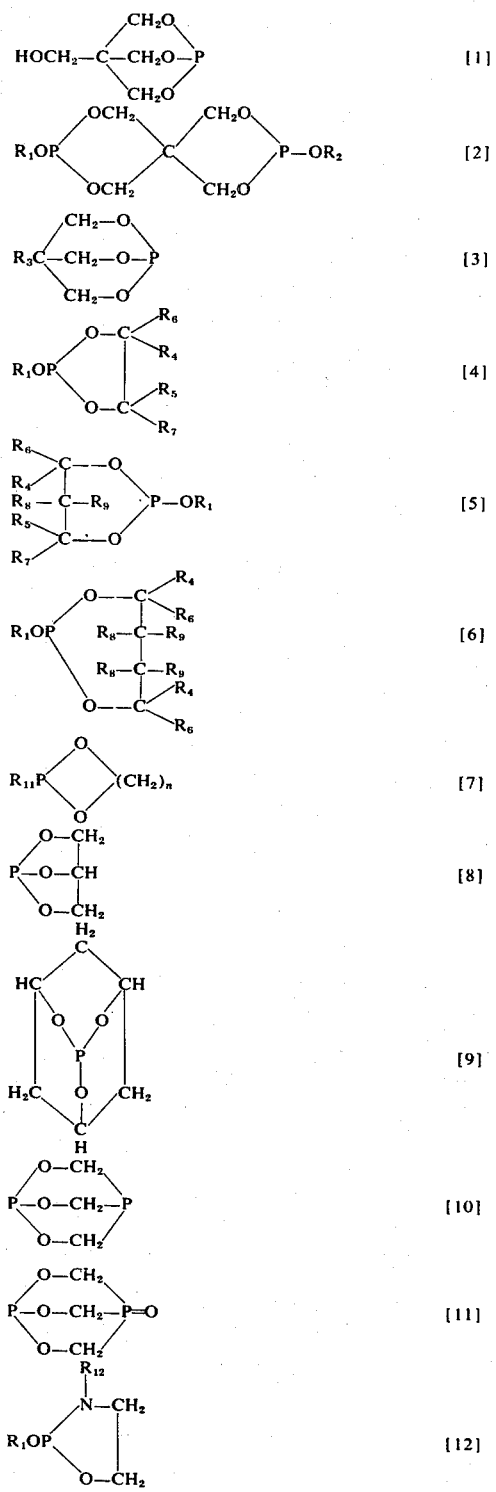

Compound (1) is pentaerythritol phosphite. It can be self polymerized to form a phosphonate by heating at a temperature of 160° to 250°C for sufficient time, e.g. heating for 16 hours at 195°–200°C. A viscous prepolymer can be formed by heating bulk monomer, e.g. for ½ to ¾ hours at 195°–200°C.

The heating of the pentaerythritol phosphite monomer to form a polymer must be for a substantial period of time. Thus, a flash distillation as in Emmons U.S. Pat. No. 3,155,703 Example 2 does not destroy the crystalline monomer. A representation of the polymerization reaction is:

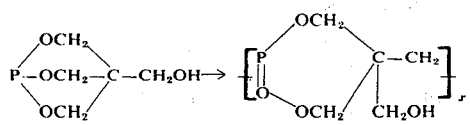

In the formulae where more than one R group is present the groups can be the same or different. In the formulae $R_1$ and $R_2$ can be alkyl, e.g. of 1 to 18 carbon atoms such as methyl, ethyl, propyl, butyl, sec.butyl amyl, 2-ethylhexyl, decyl, isodecyl, dodecyl or octadecyl, or alkenyl, e.g. of 3 to 18 carbon atoms such as allyl, methallyl, crotyl or oleyl, or aralkyl, e.g. benzyl. $R_3$ can be alkyl of 1 to 17 carbon atoms, usually of 1 to 2 carbon atoms, $R_4$, $R_5$, $R_6$, $R_7$, $R_8$ and $R_9$ can be hydrogen or lower alkyl, e.g. alkyl of 1 to 4 carbon atoms such as methyl, ethyl, propyl, and butyl, preferably $R_4$, $R_5$, $R_6$, $R_7$, $R_8$ and $R_9$ are hydrogen or not over one group attached to a single carbon atom is methyl. $R_{11}$ can be aryl, e.g. phenyl or tolyl or alkyl of 1 to 18 carbon atoms and n is 1 or 2. $R_{12}$ can be alkyl of 1 to 18 carbon atoms, e.g. methyl, ethyl propyl, isopropyl, butyl, octyl, decyl, dodecyl or octadecyl.

The starting materials of formulae (1) through (12) are all old materials.

Examples of compounds within formula (2) are dimethyl pentaerythritol diphosphites, diethyl pentaerythritol diphosphite, methyl ethyl pentaerythritol diphosphite, dipropyl pentaerythritol diphosphite, dibutyl pentaerythritol diphosphite, di sec. butyl pentaerythritol diphosphite, diamyl pentaerythritol diphosphite, di-(2-ethylhexyl) pentaerythritol diphosphite, bis decyl pentaerythritol diphosphite, dilauryl pentaerythritol diphosphite, distearyl pentaerythritol diphosphite, dibenzyl pentaerythritol diphosphite, diallyl pentaerythritol diphosphite, dimethallyl pentaerythritol diphosphite, dioleyl pentaerythritol diphosphite.

Examples of compounds within formula (3) are trimethylolethane phosphite, trimethylolpropane phosphite, trimethylolbutane phosphite, trimethylolisobutane phosphite, trimethylohexane phosphite, trimethylolheptadecane phosphite.

Examples of compounds within formula (4) are methyl ethylene phosphite, ethyl ethylene phosphite, propyl ethylene phosphite isodecyl ethylene phosphite, octadecyl ethylene phosphite, allyl ethylene phosphite, benzyl ethylene phosphite, oleyl ethylene phosphite 1-methylethylene methyl phosphite, 2-sec. butoxy-1,3,2-dioxaphosphorinane, 2-octoxy-1,3,2-dioxaphosphorinane, 2-decoxy-1,3,2-dioxaphosphorinane, 2-isodecoxy-1,3,2-dioxaphosphorinane, 2-octadecoxy-1,3,2-dioxaphosphorinane, 2-benzyloxy-1,3,2-dioxaphosphorinane, 2-allyloxy-1,3,2-dioxaphosphorinane, 2-oleyloxy-1,3,2,-dioxaphosphorinane, 2-methoxy-4-propyl-5-ethyl-1,3,2-dioxaphosphorinane, 2-methoxy-5-ethyl-5-methyl-1,3,2-dioxaphosphorinane, 2-allyloxy-5-ethyl-5-methyl-1,3,2-dioxaphosphorinane, 2-ethoxy-4-methyl-1,3,2-dioxaphosphorinane, 2-methoxy-5,5-diethyl-1,3,2-dioxaphosphorinane, 2-methoxy-4,4,6-trimethyl-1,3,2-dioxaphosphorinane, 2-octadecoxy-5, 5-dimethyl-1,3,2-dioxaphosphorinane.

Examples of compounds within formula (6) are methyl tetramethylene phosphite, ethyl tetramethylene phosphite, 1-methylethylene isodecyl phosphite 1-methylethylene octadecyl phosphite, 1,2-dimethylethylene decyl phosphite, 1,2-dimethylethylene methyl phosphite, 1,2,-dimethylethylene ethyl phosphite, 1,1,2,2-tetramethylethylene methyl phosphite, 1,1,2,2-tetramethylethylene decyl phosphite, 1-propylethylene methyl phosphite.

Examples of compounds within formula (7) are phenyl ethylene phosphonite, methyl ethylene phosphonite, ethyl ethylene phosphonite, also phenyl trimethylene phosphite methyl trimethylene phosphonite etc.

Examples of compounds within formula (5) are 2-methoxy-1,3,2-dioxaphosphorinane, 2-ethoxy-1,3,2-dioxaphosphorinane, 2-isopropoxy-1,3,2-dioxaphosphorinane, tetramethylene phosphite, allyl tetramethylene phosphite benzyl tetramethylene phosphite, oleyl tetramethylene phosphite octadecyl tetramethylene phosphite.

Examples of compounds within formula (12) are 2-methoxy 3-methyl-1,3,2-oxa-aza-phospholane, 2-methoxy-3-ethyl-1,3,2-oxa-aza-phospholane, 2-methoxy-3-propyl-1,3,2-oxa-aza-phospholane, 2-methoxy-3-butyl-1,3,2-oxa-aza-phospholane, 2-methoxy-3-hexyl-1,3,2-oxa-aza-phospholane, 2-methoxy-3-octadecyl-1,3,2-oxa-aza-phospholane, 2-ethoxy-3-methyl-1,3,2-oxa-aza-phospholane, 2-allyloxy-3-propyl-1,3,2-oxa-aza-phospholane, 2-benzyloxy-3-propyl-1,3,2-oxa-aza-phospholane.

The alcohols which react with the above phosphorus compounds of formulae (1) through (12) have the formula $R_{13}OH$ where $R_{13}$ is n-alkyl of 1 to 4 carbon atoms, allyl, benzyl or 2,3-dibromopropyl. When the phosphite of formula (5) has a neoalkyl group, e.g. neopentyl methyl phosphite is reacted with the alcohol $R_{13}OH$ and at least one of $R_1$ and $R_{13}$ is methyl, the product is the cyclic phosphonate

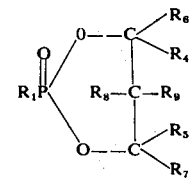

(both $R_8$ and $R_9$ are alkyl) even when only a small amount of the compound $R_{13}OH$ is employed, e.g. 0.05 mol per mol of the alcohol per mol of cyclic phosphite.

When a compound of formula (2) is reacted with the alcohol $R_{13}OH$ and $R_1$ and $R_2$ are not methyl then the C-P bonds formed will be from $R_1$ and $R_2$. When $R_1$ and $R_2$ are both methyl then P—C bond is from the alcohol $R_{13}OH$ except that when $R_{13}OH$ is butyl alcohol then in the formula of the compound formed:

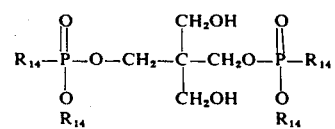

three of the $R_{14}$ groups are butyl and one is methyl.

The polymeric phosphonates formed are usually linear except the polymeric phosphonates formed from pentaerythritol phosphite are normally cross-linked.

The reaction for polymer formation using small amounts of the compound $HOR_{15}$—$OH$ where $R_{15}$ is and alkylene group of at least 2 carbon atoms, e.g. 2 to 10 carbon atoms, as follows:

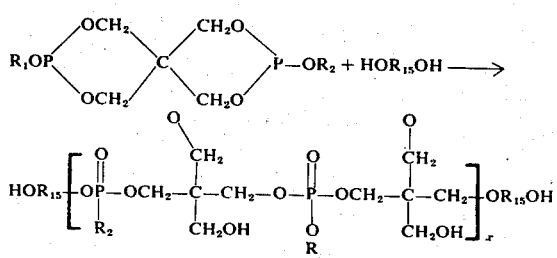

where $x$ indicates the number of repeating units. It should be realized that either $R_1$ or $R_2$ can be directly bonded to phosphorus to form the phosphonate units.

Pentaerythritol phosphite using a small amount of $R_{13}OH$ or $HOR_{15}OH$ homopolymerizes. A representation of such reaction is as follows:

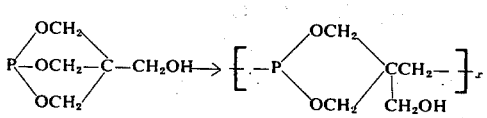

where $x$ is the number of repeating units.

Unless otherwise indicated all parts and percentages are by weight.

Further illustrative examples of the present invention are set forth below.

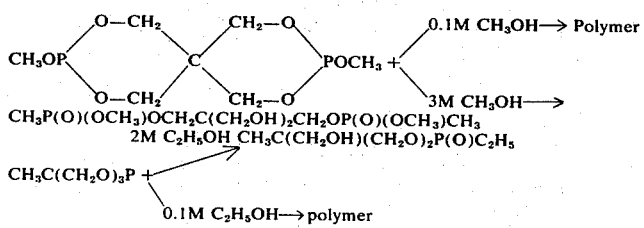

In certain cases, where the cyclic phosphite contains a methoxy group, isomerization to the phosphonate is the major product. This is also true if the alcohol used for the Arbuzov type reaction is methyl. This probably proceeds through ring-opening with subsequent methanol elimination:

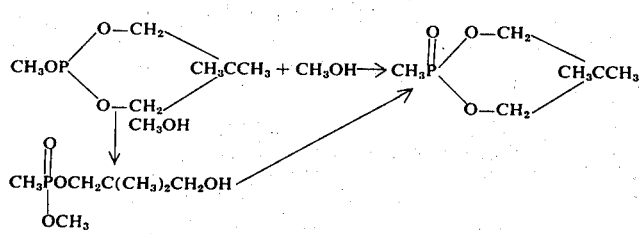

Where the group is not methyl, e.g. it is allyl or ethyl there is obtained ring-opening with subsequent polymerization.

EXAMPLE 1

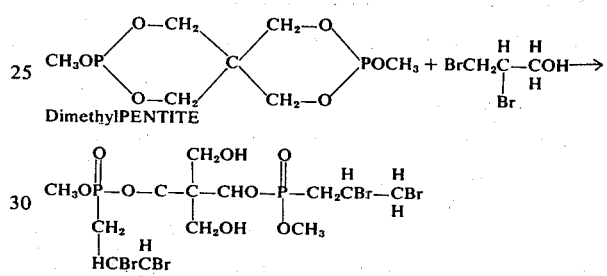

52.5g (0.204 mol) of (I) was heated in a closed vessel with 205 ml (2.24 mols) of n-butanol at 125°–130°C for 20 hours. At the end of this period a test for phosphite indicated that 98% of the phosphite had been converted to a phosphonate. Evaporation of the excess butanol gave a 95% yield of colorless liquid which had an OH value of 240. The theoretical value for (II) is 238. Methanol was detected by GPC, indicating that some transesterification had occurred, probably before ring-opening.

EXAMPLE 2

64 g (0.25 mol) of dimethylPENTITE was added to 218 g (1.0 mol) of 2,3-dibromopropanol. The mixture was heated to 125°C, when it started to exotherm to 130°C. It was held at this temperature for 3 hours. A test for phosphite indicated that reaction was completed. The excess of dibromopropanol was stripped at 100°C/0.5mm. The residue was a viscous liquid which weighed 170 g. NMR indicated that the product was predominantly free of neohalogen atoms, indicating that the alcohol had reacted preferentially to the bromine in the ring-opening operation.

EXAMPLE 3

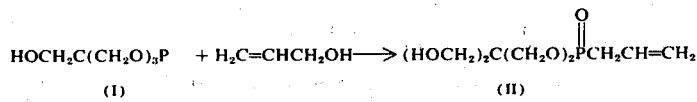

0.1 mol of pentaerythritol phosphite was reacted with 0.2 mol of allyl alcohol for 3 hours at 130°C. The test for phosphite indicated that the reaction was complete at the end of this period. After the excess allyl alcohol had been stripped, a viscous liquid remained. Hydroxyl value and NMR showed the product to be consistent with Structure II. The yield was quantitative.

EXAMPLE 4

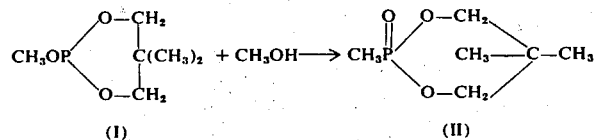

0.2 mol of neopentyl glycol methyl phosphite (I) was heated with 0.01 mol methanol for 15 hours at 190°C in a sealed tube. The contents of the tube had solidified to a crystalline solid identified as the cyclic phosphonate (II). The yield was quantitative.

EXAMPLE 5

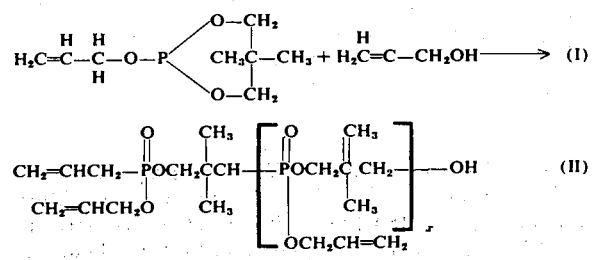

0.2 mol of (I) and 0.01 mol of allyl alcohol were heated to 200°C for 12 hours. At the end of this period a colorless, tough resin resulted. The resin softened at 180°C and was insoluble in the common solvents.

EXAMPLE 6

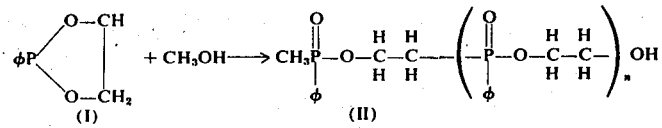

0.2 mol of (I) was heated in a sealed glass tube with 0.005 mol of methanol for 12 hours at 200°C. The product was a clear plastic which melted above 170°C. It was insoluble in most common solvents. Reflectance I.R. scan showed the presence of P=O bonds.

EXAMPLE 7

0.2 mol of dimethyl pentaerythritol diphosphite and 0.01 mol of hexamethylene glycol were heated at 200°C for 12 hours to produce a resinous polymer according to the equation:

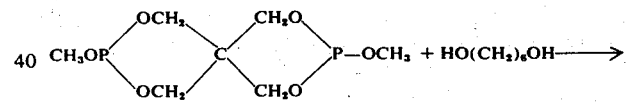

EXAMPLE 8

The adhesive properties to glass of polymers of pentaerythritol phosphite (PE phosphite), the monomer having the formula

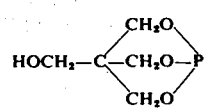

are demonstrated in the following table:

TABLE I

| | Adhesive Properties on Glass of PE Phosphite Polymer | | | |
| --- | --- | --- | --- | --- |
| | Flex Strength of "butt" Bond | | Shear Strength of "lap" Bond | |
| ADHESIVE | psi | COMMENTS | psi | COMMENTS |
| Contact Cement[a] | 5½ | | < 10 | Bond broke during handling |
| General Purpose Cement[b] | 21 | | 480 | |
| Epoxy[c] | 102 | Bond and glass failure | >510 | Glass failure |
| From PE Phosphite Monomer[d] | <2 | Bond broke during handling | >385 | Glass Failure |
| From PE Phosphite Prepolymer[e] - Cured 2 hrs. | 210 | Clean bond failure | 554 | Glass and bond failure |
| From PE Phosphite | >510 | Glass failure occurred | >540 | Glass failure |

TABLE I-continued

Adhesive Properties on Glass of PE Phosphite Polymer
Flex Strength of "butt" Bond        Shear Strength of "lap" Bond

| ADHESIVE | psi | COMMENTS | psi | COMMENTS |
|---|---|---|---|---|
| Prepolymer Cured 16 hours | | diagonally through bond | | | a. Goodyear Pli-O-Bond
b. DuPont Duco Cement
c. GE Electronics two part Epoxy
d. Monomer placed between glass faces and cured under $N_2$ for 16 hours at 195–200°C
e. Viscous Prepolymer prepared by heating bulk monomer ½–¾hours at 195–200°C under $N_2$ The process of the invention can comprise, consist essentially of or consist of the steps set forth.

The monomeric phosphonates derived from compounds of formula (2) by reacting one mole thereof with two moles of the alcohol $R_{13}OH$ have the formula

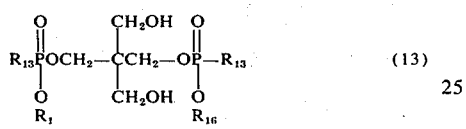
(13)

where $R_1$ and $R_{13}$ are as defined above and $R_{16}$ is $R_1$ except that when $R_{13}$ is butyl then $R_{16}$ is butyl.

The monomeric phosphonates derived from the compounds of formula (3) by reacting one mole thereof with one mole of the alcohol $R_{13}OH$ have the formula:

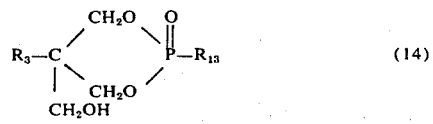
(14)

where $R_3$ and $R_{13}$ are as defined above.

The monomeric phosphonates derived from the compounds of formulae (4) and (5) by reacting one mole thereof with one mole of the alcohol $R_{13}OH$ have the formula

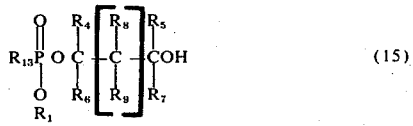
(15)

where $R_1$, $R_{13}$, $R_4$, $R_5$, $R_6$, $R_7$, $R_8$ and $R_9$ are as defined above and s is 0 or 1 except that when $R_8$ and $R_9$ are both alkyl and $R_1$ and $R_{13}$ are methyl the formula of the phosphonate is:

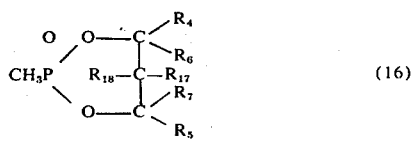
(16)

where $R_{17}$ and $R_{18}$ are both alkyl.

What is claimed is:

1. A monomeric phosphonate having a formula selected from the group consisting of:

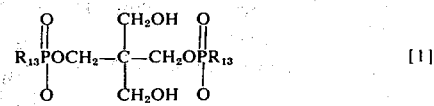
[1]

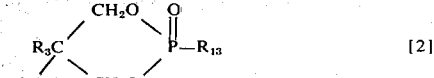
[2]

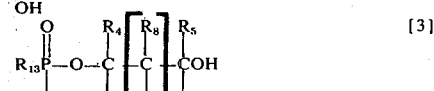
[3]

or

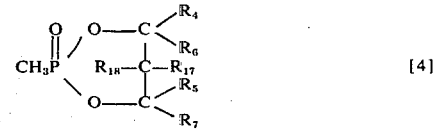
[4]

where $R_1$ is alkyl, alkenyl or aralkyl, $R_{13}$ is normal alkyl of 3 to 4 carbon atoms or the residue of a monohydric alcohol having a pKa below that of n-propyl alcohol from which the OH is removed, $R_{16}$ is as defined for $R_1$ or $R_{13}$, $R_3$ is alkyl of 1 to 17 carbon atoms or hydroxymethyl, $R_4$, $R_5$, $R_6$, $R_7$, $R_8$ and $R_9$ are hydrogen or lower alkyl and $R_{17}$ and $R_{18}$ are lower alkyl and s is 0 or 1.

2. A phosphonate according to claim 1 where $R_{13}$ is n-alkyl of 1 to 4 carbon atoms, allyl, benzyl or 2,3-dibromopropyl.

3. A phosphonate according to claim 2 having formula (1).

4. A phosphonate according to claim 3 wherein $R_{16}$ is methyl, ethyl, allyl, benzyl or 2,3-dibromopropyl.

5. A phosphonate according to claim 4 wherein $R_1$ is methyl.

6. A phosphonate according to claim 3 where $R_{13}$ and $R_{16}$ are butyl and $R_1$ is methyl.

7. A phosphonate according to claim 3 wherein $R_1$, $R_{13}$ and $R_{16}$ are all methyl.

8. A phosphonate according to claim 3 wherein $R_{13}$ is allyl or 2,3-dibromopropyl, $R_1$ is methyl and $R_{16}$ is methyl.

9. A phosphonate according to claim 8 where $R_{13}$ is allyl.

10. A phosphonate according to claim 8 where $R_{13}$ is 2,3-dibromopropyl.

11. A phosphonate according to claim 2 having formula (2).

12. A phosphonate according to claim 11 where $R_3$ is alkyl of 1 to 2 carbon atoms.

13. A phosphonate according to claim 12 where $R_{13}$ is methyl, ethyl, allyl, benzyl or 2,3-dibromopropyl.

14. A phosphonate according to claim 11 where $R_3$ is hydroxymethyl.

15. A phosphonate according to claim 14 wherein $R_{13}$ is methyl, ethyl, allyl, benzyl or 2,3-dibromopropyl.

16. A phosphonate according to claim 2 having formula (3).

17. A phosphonate according to claim 16 where $R_8$ is hydrogen.

18. A phosphonate according to claim 17 wherein $R_{13}$ is methyl, ethyl, allyl, benzyl or 2,3-dibromopropyl.

19. A phosphonate according to claim 18 where s is 0.

20. A phosphonate according to claim 19 where $R_4$, $R_5$, $R_6$ and $R_7$ are all hydrogen.

21. A phosphonate according to claim 18 where s is 1.

22. A phosphonate according to claim 2 having formula (4).

23. A phosphonate according to claim 22 where $R_4$, $R_5$, $R_6$ and $R_7$ are all hydrogen and $R_{17}$ and $R_{18}$ are both methyl.

24. The polymeric phosphonate of:

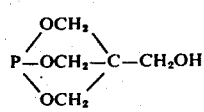

having the repeating unit:

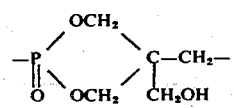

* * * * *

UNITED STATES PATENT AND TRADEMARK OFFICE
CERTIFICATE OF CORRECTION

PATENT NO. : 3,978,166

DATED : August 31, 1976

INVENTOR(S) : HECHENBLEIKNER

It is certified that error appears in the above-identified patent and that said Letters Patent are hereby corrected as shown below:

Column 9, formula (15) on line 50 the formula should read

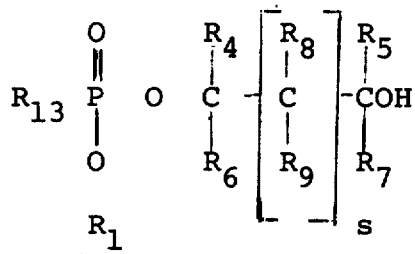

Column 9, formula (16) on line 60 the formula should read

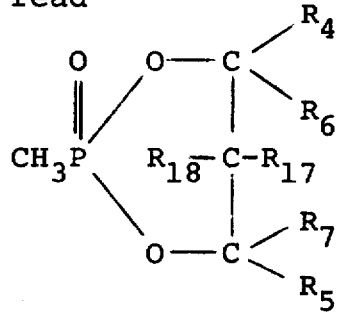

UNITED STATES PATENT AND TRADEMARK OFFICE
CERTIFICATE OF CORRECTION

PATENT NO. : 3,978,166

DATED : August 31, 1976

INVENTOR(S) : HECHENBLEIKNER

It is certified that error appears in the above-identified patent and that said Letters Patent are hereby corrected as shown below:

Claim 1 column 10 formula (3) should read

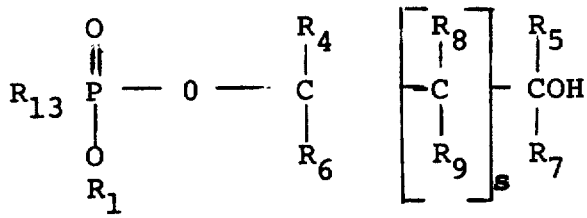

Signed and Sealed this

Twentieth Day of March 1979

[SEAL]

Attest:

RUTH C. MASON
Attesting Officer

DONALD W. BANNER
Commissioner of Patents and Trademarks